United States Patent [19]

Katsaros et al.

[11] Patent Number: 5,226,883
[45] Date of Patent: Jul. 13, 1993

[54] FLASHBACK VENTILATION CAP

[75] Inventors: Georges Katsaros, Liege; Giancarlo Polese, Olne, both of Belgium

[73] Assignee: Sherwood Medical Company, St. Louis, Mo.

[21] Appl. No.: 860,911

[22] Filed: Mar. 31, 1992

[51] Int. Cl.⁵ .................. A61M 5/00; A61M 5/178
[52] U.S. Cl. ...................... 604/110; 604/111; 604/168; 604/900
[58] Field of Search ............... 604/110, 126, 128, 129, 604/161, 168, 256, 283, 284, 324, 333, 415, 900, 905, 111; 128/912, 917; 220/266, 270, 272; 285/3, 4

[56] References Cited

U.S. PATENT DOCUMENTS

| | | | |
|---|---|---|---|
| 3,859,998 | 1/1975 | Thomas et al. | 128/214.4 |
| 4,020,835 | 5/1977 | Nordstrom et al. | 128/214.4 |
| 4,046,144 | 9/1977 | McFarlane | 128/214.4 |
| 4,193,399 | 3/1980 | Robinson | 128/214.4 |
| 4,207,870 | 6/1980 | Eldridge | 128/766 |
| 4,226,236 | 10/1980 | Genese | 128/218 M |
| 4,314,555 | 2/1982 | Sagae | 128/217.4 |
| 4,464,177 | 8/1984 | McGaughey et al. | 604/168 |
| 4,487,605 | 12/1984 | McGaughey et al. | 604/168 |
| 4,631,056 | 1/1986 | Dye | 604/111 |
| 4,692,150 | 9/1987 | Cianci et al. | 604/111 |
| 4,834,706 | 5/1989 | Beck et al. | 604/111 |
| 4,899,903 | 2/1990 | Miyasaka et al. | 220/266 |
| 4,911,696 | 3/1990 | Miyasaka et al. | 604/244 |
| 4,917,671 | 4/1990 | Chang | 604/168 |
| 5,032,116 | 7/1991 | Peterson et al. | 604/168 |
| 5,066,284 | 11/1991 | Mersch et al. | 604/168 |
| 5,104,379 | 4/1992 | Nakamura et al. | 604/111 |

Primary Examiner—Randall L. Green
Assistant Examiner—K. Reichle
Attorney, Agent, or Firm—Gene B. Kartchner; Montgomery W. Smith; David A. Warmbold

[57] ABSTRACT

A ventilation cap for a flashback chamber is formed of a hollow elongate cylindrical body of polymeric material and includes a proximal opening which is blocked by a venting material such as a hydrophobic filter, and a distal opening which is sized to allow an extension of the flashback chamber to be inserted therein for airtight connection therewith. The elongate body of the ventilation cap has a tear strip formed therein by a pair of generally parallel score lines. The cap is affixed to the flashback chamber so as to allow air to pass from the flashback chamber through the vent as blood fills the flashback chamber, while preventing blood from passing through the vent. When it is desired to attach other apparatus to the extension of the flashback chamber, the tear strip, which may have a pull tab integrally formed therewith, is torn away from the elongate body to destroy the airtight seal between the flashback extension and the cap. Once the tear strip has been pulled away from the body of the cap, the cap can be easily removed from the extension without the creation of vacuum forces which would tend to cause spillage of blood from the flashback chamber.

20 Claims, 2 Drawing Sheets

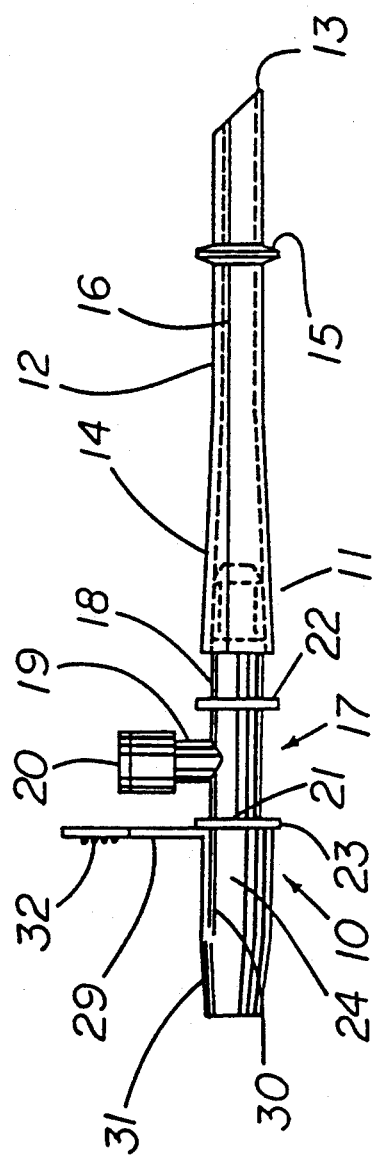
FIG. 1
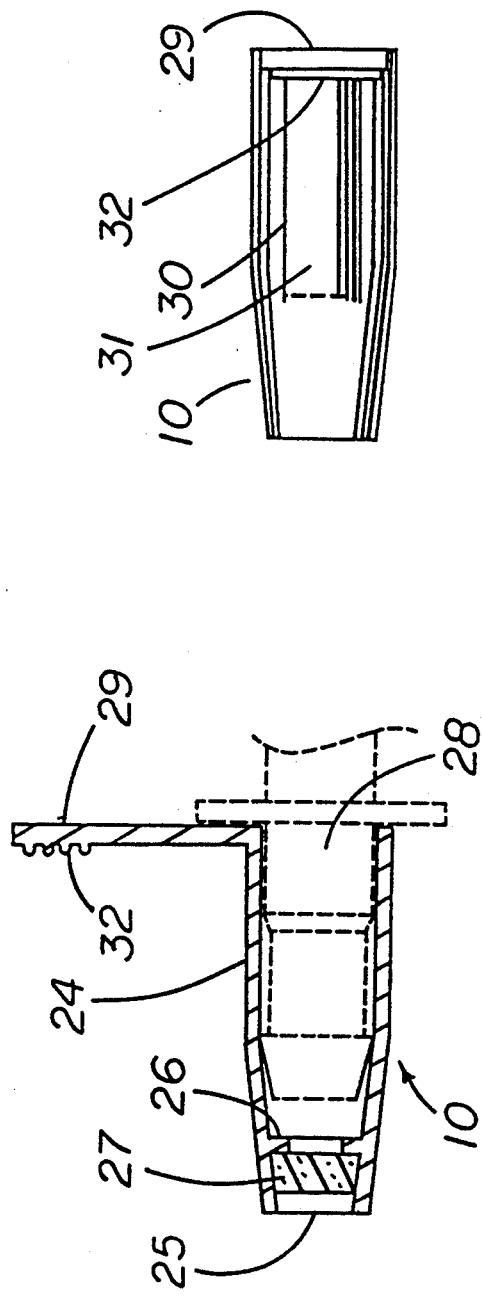
FIG. 3
FIG. 2

FLASHBACK VENTILATION CAP

BACKGROUND OF THE INVENTION

1. Field of the Invention

This invention relates to a ventilation cap for a fluid passage device, such as a perfusion cannula intended for the passage of blood. More specifically, the present invention relates to a ventilation cap which includes a filter which allows air to be vented out of the device during a flashback-type insertion procedure, while at the same time preventing fluid flow from the device. The present invention further relates to a ventilation cap which is designed to allow simplified detachment and removal of the cap from the device while at the same time minimize incidental blood spillage during removal.

2. Prior Art

Introducer needles, catheters, cannulas and other tubular intravenous devices are commonly used for the passage of body fluids, such as blood, into and out of a patient's body. Such devices often include means such as a flashback chamber for observing the presence of blood during insertion thereof. The "flashback" of blood is an indication of the proper placement of the device in the patient. Devices intended to be placed in fluid flow connection with a vein or artery often employ a transparent flashback chamber into which blood can freely flow when the tip of the device is properly placed within the vein or artery of the patient. The flashback chamber is generally located so as to be in direct fluid communication with the tip of the device intended to be inserted into the body, and to be visually monitored by the medical worker performing the placement procedure. During placement, when the tip of the device accesses a blood flow passage in the body such as a vein or artery, blood will flow through the device into the transparent flashback chamber and become visually apparent to the medical worker, thus indicating proper placement of the tip. Once a device is properly placed in the patient and secured, it is often necessary to connect it to other medical apparatus needed to carry out a desired surgical procedure.

It is very important in the operation of the flashback chamber that means be included therein which permit air to leave the chamber as a result of the entry of blood therein, but which also prevent blood from passing through the vent and exiting the chamber. Due to present concerns about infection by blood-carried diseases such as AIDS and hepatitis, devices which are designed to prevent blood spillage have become highly desirable for use in these types of placement procedures. For example, U.S. Pat. No. 5,032,116 to Peterson et al. discloses a flashback plug which includes a vent membrane of hydrophobic filter material mounted across an internal passage. The plug is adapted to be engaged in airtight communication with a flashback chamber of a cannula insertion device to allow passage of air out of the chamber while preventing the passage of blood. U.S. Pat. No. 5,066,284 to Mersch et al. discloses a ventilation plug adapted to be inserted into a flashback chamber, the plug allows ventilation of air from the flashback chamber through a plurality of air vents drilled by a laser. The air vents are too small to allow passage of blood therethrough. U.S. Pat. No. 4,917,671 to Chang discloses a ventilation plug for a flashback chamber which uses a porous insert to allow ventilation of air and prevent the passage of blood. U.S. Pat. No. 3,859,998 to Thomas et al. discloses a ventilation plug which employs a slitted diaphragm for venting air from the flashback chamber while preventing passage of blood therethrough. U.S. Pat. No. 4,193,399 to Robinson discloses a ventilation plug which is formed entirely of porous plastic material which allows passage of air but prevents the passage of blood.

Although many approaches to ventilation of flashback chambers have been proposed, several drawbacks with the prior art devices still remain. Specifically, the prior art flashback chamber ventilation devices fail to address the problem of accessing the flashback chamber after flashback has occurred without causing a spillage of blood from the chamber in order to connect the device to another medical apparatus, without causing a spillage of blood from the chamber. Prior art flashback ventilation devices are necessarily secured in an airtight manner to the flashback chamber, and are therefore difficult to remove therefrom in order to allow attachment of other medical apparatus. Since the connection between the ventilation plug and the flashback chamber is necessarily extremely tight, it is often difficult to remove the plug without developing substantial vacuum forces within the flashback chamber which cause spillage of blood therefrom when the plug is removed.

Therefore, a need exists in the art to develop a ventilation cap which is designed to avoid spillage of blood from a flashback chamber when removed. There is further a need in the art to develop a ventilation cap in which the seal between the cap and the flashback chamber which hold the cap in airtight connection therewith, can be destroyed prior to removal of the cap from the flashback chamber. These improvements allow a decrease the force necessary to withdraw the cap from the flashback chamber, to prevent the generation of vacuum forces within the flashback chamber during removal and simplify the removal procedure.

OBJECTS AND SUMMARY OF THE INVENTION

It is an object of the present invention to provide a ventilation cap for a medical device which allows the passage of air therethrough but prevents the passage of fluid.

It is further an object of the present invention to provide a ventilation cap for a medical device which is easily removable from the medical device It is further an object of the present invention to provide a ventilation cap which allows the airtight seal thereof against the medical device to be destroyed prior to removal of the cap therefrom.

It is another object of the present invention to provide a ventilation cap for a medical device which can be removed from the medical device without causing the generation of vacuum forces therein.

Briefly, and in general terms, the present invention provides a ventilation cap for ventilation of air from a medical device while preventing fluid from escaping, and also provides a structural design which simplifies removal of the ventilation cap from the medical device, and significantly reduces the likelihood of fluid spillage from the device during removal of the ventilation cap.

In a presently preferred embodiment, by way of example and not necessarily by way of limitation, a ventilation cap made in accordance with the principles of the present invention includes a hollow elongate cylindrical body preferably molded of a polymeric material, including a distal end opening for engagement over a cylindrical extension of a flashback chamber of a perfusion cannula in an airtight manner, and a proximal end opening which is blocked by a vent material, such as a hydrophobic filter, to allow the passage of air therethrough but prevent the passage of blood. The venting material may be held in position in the distal end opening of the elongate body in any well known manner, such as by a friction fit, adhesive, or the like, and functions simultaneously as a passageway for air and a barrier for blood or other body fluids.

The cap further includes a pair of parallel longitudinally formed score lines which extend along the exterior surface of the elongate body from the proximal end opening thereof to approximately the position of the venting material. The portion of the elongate body between the score lines is formed into a tear strip which can be separated from the remainder of the elongate body when it is desired to destroy the airtight seal between the cap and the flashback chamber extension and remove the cap for attachment of other medical apparatus. The tear strip may include a pull tab integrally formed therewith, preferably at the proximal end thereof, which extends away from the elongate body and facilitates tearing of the tear strip along the score lines.

In use, the preferred embodiment of the ventilation cap of the present invention is affixed over an extension of a flashback chamber of a perfusion cannula in an airtight manner. During insertion of the cannula tip into a patient's vein or artery, the ventilation cap functions to allow passage of air through the venting material while preventing the passage of blood and other fluids. Upon completion of the insertion procedure, the cannula is clamped to prevent further blood flow therethrough and the pull tab of the cap is pulled to cause the tear strip to tear away from the elongate body of the cap along the score lines thereof until the airtight seal between the cap and the flashback chamber extension is broken. The cap can then be removed from the flashback chamber extension without generating a vacuum force within the flashback chamber which would, if present, draw blood therefrom and cause spillage. Removal of the cap from the flashback chamber can then be accomplished either by continued pulling of the pull tab in a direction away from the flashback chamber extension, or by downward rotation of the cap relative to the extension to cause the extension to rotate upwardly through the opening in the elongate body left by the removal of the tear strip therefrom. In either case, the generation of a vacuum force which would pull blood from the flashback chamber will be avoided. The cannula can then be attached to another medical apparatus such as a blood oxygenation machine, in preparation for its intended use, and the cannula can be unclamped to resume blood flow therethrough These and other objects and advantages of the present invention will become apparent from the following more detailed description thereof, when taken in conjunction with the accompanying drawings in which like elements are identified with like numerals throughout.

BRIEF DESCRIPTION OF THE DRAWINGS

FIG. 1 is a side view of a ventilation cap formed in accordance with the principles of the present invention as it would appear fitted to an extension of a flashback chamber of a perfusion cannula;

FIG. 2 is a cross-sectional view of a ventilation cap formed in accordance with the principles of the present invention with the extension of the flashback chamber shown in dashed lines;

FIG. 3 is a top view of a ventilation cap formed in accordance with the principles of the present invention;

DETAILED DESCRIPTION

Figure 5:
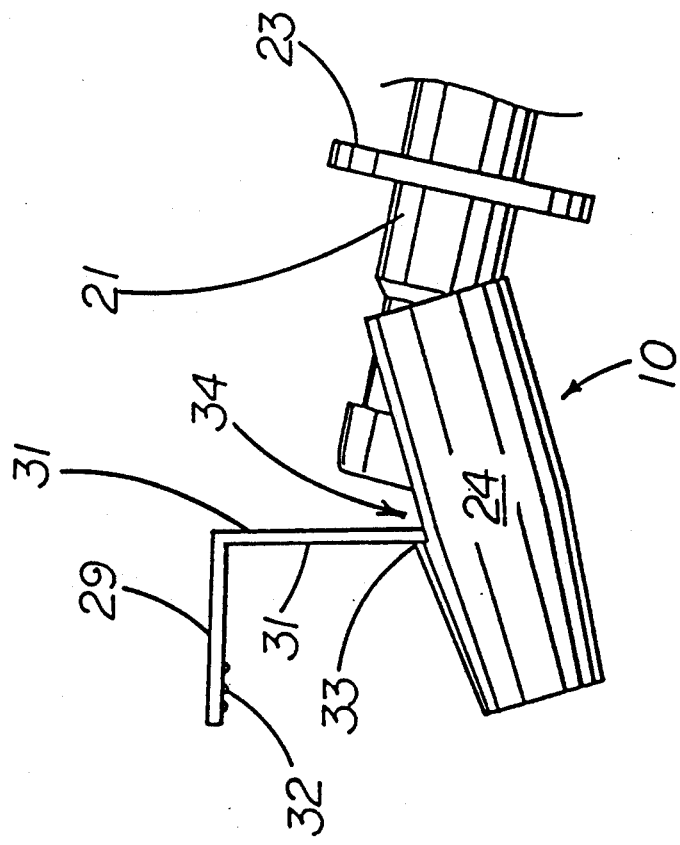
FIG. 5 is a side view of a ventilation cap formed in accordance with the principles of the present invention and the flashback chamber, showing a preferred method of removal of the ventilation cap therefrom.

As shown in the exemplary drawings for the purposes of illustration, an embodiment of a ventilation cap made in accordance with the principles of the present invention, referred to generally by the reference numeral 10, is provided for ventilation of, and simplified removal from, a flashback chamber of a fluid passage device such as the perfusion cannula device 11.

More specifically, as shown in FIG. 1, the device 11 includes a cannula 12 formed of a relatively soft flexible polymeric material The cannula 12 is formed with an elongate fluid flow passage extending from the distal tip 13 to the proximal end opening 14 thereof If desired, the cannula 12 may include a radiopaque placement ring 15 and a radiopaque strip 16 to aid the medical worker in placing and securing the cannula 12 to a patient.

A flashback chamber 17 of the device 11 preferably takes the form of a T-shaped connector made from a relatively rigid transparent polymeric material. The chamber 17 includes an extension 18 which is sized to be insertable into the proximal end opening 14 of the cannula 12 in fluidtight connection therewith. The extension 18 includes a stop ring 22 located thereon which limits the depth of insertion of the extension 18 into the cannula 12.

The flashback chamber also includes an extension 19 which extends generally perpendicularly to extension 18 (and perpendicularly to the longitudinal axis of the cannula 12). The extension 19 may include a port cover 20 which is designed to be removable to allow access to the interior of the flashback chamber 17 by a syringe or the like for the purpose of injecting or withdrawing fluid therefrom.

An extension 21 is also formed from the flashback chamber 17, and extends in the opposite direction of extension 18 contiguously with the longitudinal axis of the cannula 12. A stop ring 23 is located on extension 21 and functions to prevent over-insertion of the extension 21 into the ventilation cap 10.

As best shown in FIG. 2, the ventilation cap 10 includes a hollow elongate cylindrical body 24 which is preferably formed of a polymeric material. The body 24 forms a proximal end opening 25 which is partially restricted by an integrally formed base ring 26, and a distal end opening 28. A venting material such as a hydrophobic filter 27 is inserted into the proximal end opening 25 until it is positioned in abutting relationship with the base ring 26. The filter 27 may be maintained within the opening 25 in any well-known manner such as by friction fit, adhesive, or the like. The distal end opening 28 is sized to be insertable over the extension 21 of the flashback chamber 17 to form an airtight fit therewith.

As best shown in FIG. 3, the elongate cylindrical body 24 includes a pair of score lines 30 which extend parallel to each other in a longitudinal direction along the body 24, from the distal end opening 28 thereof, to a position directly adjacent the filter 27 in the proximal end opening 25. The portion of the elongated cylindrical body 24 which falls between the score lines 30 is formed thereby into a tear strip 31. A pull tab 29 is preferably integrally formed with the tear strip 31 adjacent the opening 28 of the body 24, and extends away therefrom in a generally perpendicular direction. The pull tab 29 may include a gripping surface 32 thereon to assist the medical worker in firmly gripping the pull tab 29 during use.

Figure 4:
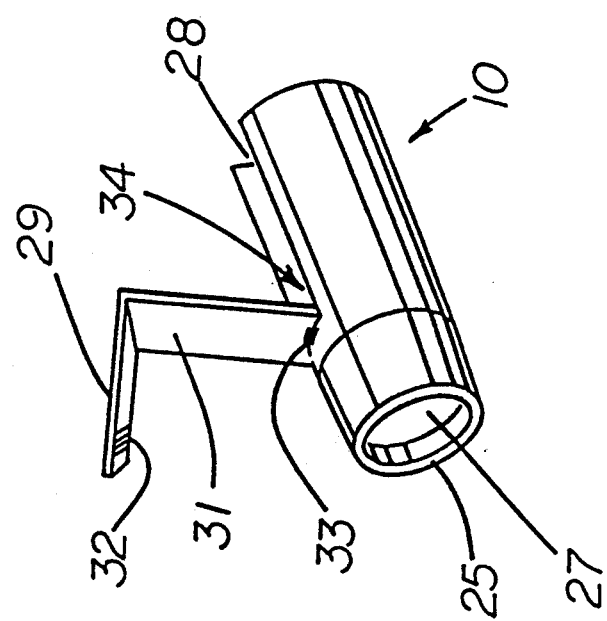
FIG. 4 is a perspective view of a ventilation cap formed in accordance with the principles of the present invention as it would appear after removal from the flashback chamber.

As shown in FIG. 4, when pull tab 29 is pulled in a direction away from the elongate cylindrical body 24, the tear strip 31 tears away from the body 24 along the score lines 30 until it reaches the tear strip baseline 33, which is located at the proximal end of the score lines 30 at a position directly adjacent the filter 27 in the proximal end opening 25. When the tear strip 31 has been separated from the body 24, it forms an elongate slot 34 which renders the remainder of the body 24 incapable of maintaining an airtight seal with the extension 21 of the flashback chamber 17.

The preferred method of operation of the ventilation cap 10 of the present invention is as follows. The cap 10 is inserted over the extension 21 of the flashback chamber 17 until the distal end opening 28 thereof is adjacent the stop ring 23 (as shown in FIG. 1). The tip 13 of the device 11 is then inserted into a patient's vein or artery until flashback occurs, meaning, until blood from the vein or artery passes through the cannula 12 into the flashback chamber 17. As blood fills the flashback chamber 17, air is displaced therefrom and passes through the filter 27. Blood may completely saturate the filter 27, thus eventually preventing any further air flow therethrough, however, blood is prevented from escaping from the interior of the chamber 17 by the filter 27. Once the medical worker has noted that flashback has occurred, a clamp, such as ordinary surgical forceps, is inserted over the cannula 12 and used to clamp the cannula 12 closed against further flow of blood. Thereafter, the cannula 12 is permanently fixed in position relative to the patient.

At this point, the device 11 is ready to be attached to another apparatus such as a blood oxygenation machine (not shown). However, since tubing from the machine must be attached to the extension 21, the ventilation cap 10 must first be removed therefrom. It is very important that removal of the ventilation cap 10 from the extension 21 not cause spillage of blood from the flashback chamber 17 which could subsequently contact and infect the medical worker or others. In order to release the ventilation cap 10 from its airtight connection with extension 21, the medical worker grips the pull tab 29 at its gripping surface 32, and pulls it away from the elongate cylindrical body 24, causing tear strip 31 to tear along score lines 30 all the way to the tear strip baseline 33. This destroys the airtight connection between extension 21 and the ventilation cap 10, and facilitates subsequent removal of the cap 10.

If desired, the medical worker may continue to pull the tab 29 away from the extension 21, thus causing the elongated cylindrical body 24 to be withdrawn therefrom, or, alternatively, a medical worker may grip the body 24 and pull it away from the extension 21 in a direction parallel to the longitudinal axis of the cannula 12. Further, if desired, a third alternative method of removing the cap 10 once the airtight seal has been broken can be performed. As shown in FIG. 5, the elongate cylindrical body 24 may be gripped and rotated relative to the extension 21 in such a manner that the extension 21 is effectively pushed through the slot 34 in the elongated cylindrical body formed as a result of the removal of the tear strip 31. In this manner, the medical worker can carefully, and in a completely controlled motion, remove the ventilation cap 10 from the extension 21, thus significantly avoiding any danger of spillage of blood from the flashback chamber 17.

Regardless of the method of removal of the cap 10 from the extension 21, once the tear strip 31 has been torn away from the body 24 down to the tear strip baseline 33, there is no further possibility of generating a vacuum force against the blood in the flashback chamber 17 as a result of removal of the cap 10 therefrom, even though the filter 27 may have been totally saturated with blood and is therefore no longer able to pass air therethrough.

It will be apparent from the foregoing that, while a particular embodiment of the invention has been illustrated and described, various modifications can be made thereto without departing from the spirit and scope of the invention. Accordingly, it is not intended that the invention be limited, except as by the appended claims.

We claim:

1. A ventilation cap for use with a medical device having insertion means for at least partial insertion into a liquid flow passage of a patient and communication of the liquid between the flow passage and the exterior of the patient, said insertion means including a hollow tube and flashback chamber means in liquid flow connection with said hollow tube for receiving a quantity of the patient's liquid to indicate proper placement of the medical device in the patient, said cap comprising:

a hollow elongate body having a proximal end opening and a distal end opening,
   means for attachment of said body to the medical device with said distal end opening in liquid communication with said flashback chamber means and with said body exterior of the patient,
   ventilation means positioned in said proximal end opening of said hollow elongate body for allowing passage of air and inhibiting passage of liquid from the interior of the medical device to the exterior of the body, and
   means for destroying said means for attachment.

2. A ventilation cap according to claim 1 wherein said means for destroying includes a tear strip.

3. A ventilation cap according to claim 2 wherein said means for destroying further includes a pair of parallel score lines which define said tear strip.

4. A ventilation cap according to claim 3 wherein said means for attaching said body to the medical device includes at least a portion of said hollow elongate body adapted to be placed over at least a portion of the medical device.

5. A ventilation cap according to claim 4 wherein said tear strip extends along said hollow elongate body from said distal end opening to a position near said ventilation means.

6. A ventilation cap according to claim 1 wherein said ventilation means includes a filter.

7. A ventilation cap according to claim 6 wherein said filter is a hydrophobic filter.

8. A ventilation cap according to claim 7 including fixation means for securing said hydrophobic filter within said proximal end opening.

9. A ventilation cap according to claim 1 wherein said means for attaching said body includes means for forming an airtight seal with the medical device.

10. A medical device having insertion means for at least partial insertion into a liquid flow passage of a patient to pass liquid therefrom to the exterior of the patient, said insertion means including a hollow tube, said device comprising:

flashback chamber means in liquid flow connection with said hollow tube for receiving a quantity of the patient's liquid, to indicate proper placement of the medical device in the patient, a ventilation cap having a hollow elongate body with a proximal end opening and a distal end opening, the distal end opening having means for attachment of said cap to said flashback chamber means and in liquid communication therewith and with the cap exterior of the patient, and the proximal end opening having ventilation means provided therein for allowing passage of air and inhibiting passage of liquid from the flashback chamber means to the exterior of the ventilation cap, and means for destroying said means for attachment.

11. A medical device according to claim 10 wherein said flashback chamber means includes a tubular extension, and said means for attachment includes means for airtight attachment of said ventilation means to said tubular extension.

12. A medical device according to claim 11 wherein said means for destroying includes a tear strip means for breaking the attachment means to allow the ventilation cap to be easily removed from said flashback chamber means.

13. A medical device according to claim 12 wherein said tear strip means is also part of said means for attachment, whereby, said tear strip means assists in forming said airtight attachment between said tubular extension and said ventilation cap when located in a first position relative to said ventilation cap, and assists in destroying said airtight attachment when located in a second position relative to said ventilation cap.

14. A method of using a ventilation cap according to claim 1 including the steps of:

attaching the cap to the medical device, partially inserting the medical device into the patient such that said insertion means thereof enters the liquid flow passage in the patient and liquid therefrom passes into the device, allowing air to exit the device through the ventilation means while preventing the passage of body liquid therethrough, clamping the medical device against further liquid communication therethrough, destroying the attachment means of the ventilation cap, and removing the ventilation cap from the medical device.

15. A method according to claim 14 wherein said step of attaching the cap to the medical device includes forming an airtight attachment between the cap and the medical device.

16. A method according to claim 15 wherein said flashback chamber means further includes a tubular extension extending away from the medical device, and said step of attaching the cap to the medical device includes attaching the cap to the extension of the flashback chamber means of the medical device.

17. A method according to claim 15 wherein said step of destroying the attachment means of the ventilation cap includes destroying the airtight attachment between the ventilation cap and the medical device.

18. A method according to claim 14 wherein said ventilation cap further includes a tear strip formed as a part of the attachment means, and said step of destroying the attachment means includes pulling the tear strip at least partially away from the attachment means.

19. A method according to claim 18 wherein said step of removing the ventilation cap includes rotating at least a portion of the medical device through an opening in the attachment means formed from the pulling of the tear strip.

20. A method according to claim 14 including the step of attaching a medical apparatus to the medical device after the cap has been removed from the medical device.

* * * * *